United States Patent [19]
Allaire et al.

[11] Patent Number: 5,447,499
[45] Date of Patent: Sep. 5, 1995

[54] WOUND DRESSING HAVING A CYLINDRICAL SHAPE FOR DEEP WOUNDS

[75] Inventors: Michael J. Allaire, Cincinnati; Michael L. Wolf, West Milton, both of Ohio

[73] Assignee: New Dimensions in Medicine, Inc., Dayton, Ohio

[21] Appl. No.: 161,860

[22] Filed: Dec. 6, 1993

Related U.S. Application Data

[63] Continuation of Ser. No. 996,013, Dec. 23, 1992, abandoned.

[51] Int. Cl.$^6$ .............................................. A61F 13/00
[52] U.S. Cl. ..................................... 602/42; 602/43; 602/48; 602/58; 602/53; 604/385.1; 604/904
[58] Field of Search ................ 602/41, 42, 43, 48, 602/53, 58, 59; 604/289, 307, 311, 328, 358, 363, 364, 372, 385.1, 904, 49, 50, 59, 54, 55, 57, 15

[56] References Cited

U.S. PATENT DOCUMENTS

| | | |
|---|---|---|
| 2,579,403 | 12/1951 | Slomowitz et al. ............ 602/43 |
| 2,603,213 | 7/1952 | Buryan ........................ 604/328 |
| 3,220,413 | 11/1965 | Sunnen ........................ 604/311 |
| 3,783,868 | 1/1974 | Bokros . |
| 3,921,632 | 11/1975 | Bardani . |
| 3,941,125 | 3/1976 | Drake . |
| 4,209,605 | 6/1980 | Hoy et al. . |
| 4,226,232 | 10/1980 | Spence . |
| 4,278,088 | 7/1981 | Reeves et al. ................. 604/15 |
| 4,393,048 | 7/1983 | Mason, Jr. et al. . |
| 4,581,028 | 4/1986 | Fox, Jr. et al. . |
| 4,657,006 | 4/1987 | Raweings et al. . |
| 4,676,782 | 6/1987 | Yamamoto et al. . |
| 4,697,622 | 10/1987 | Swift et al. . |
| 4,705,709 | 11/1987 | Vailancourt . |
| 4,755,171 | 7/1988 | Tennant . |
| 4,787,895 | 11/1988 | Stokes et al. ................ 604/358 |
| 4,792,326 | 12/1988 | Tews ............................ 604/15 |
| 4,960,415 | 10/1990 | Reinmüller . |
| 4,979,944 | 12/1990 | Luzsicza . |
| 5,154,706 | 10/1992 | Cartmell et al. ............. 604/307 |

FOREIGN PATENT DOCUMENTS

| | | |
|---|---|---|
| 0788651 | 7/1968 | Canada ......................... 604/15 |
| 547833 | 6/1993 | European Pat. Off. . |
| 2080061 | 11/1971 | France . |
| 9206639 | 4/1992 | WIPO . |

OTHER PUBLICATIONS

American Heritage Dictionary, Second College Edition, (1982), p. 1242.

Primary Examiner—Paul B. Prebilic
Attorney, Agent, or Firm—Killworth, Gottman, Hagan & Schaeff

[57] ABSTRACT

A wound dressing capable of being inserted into a deep wound found on a patient is provided. The wound dressing contains a hydrogel material capable of absorbing wound exudate emitted by a deep wound and is substantially in the form of a cylinder. A support layer is mounted within the cylinder for purposes of providing support for the hydrogel material in the wound dressing. The invention also provides a syringe for inserting and removing the wound dressing from the deep wound for which it is applicable.

12 Claims, 2 Drawing Sheets

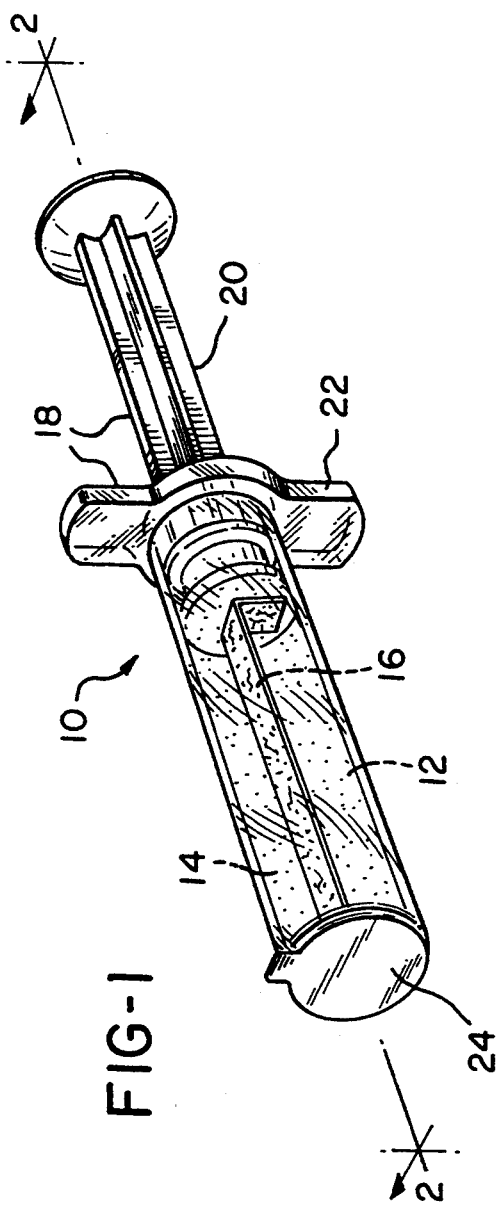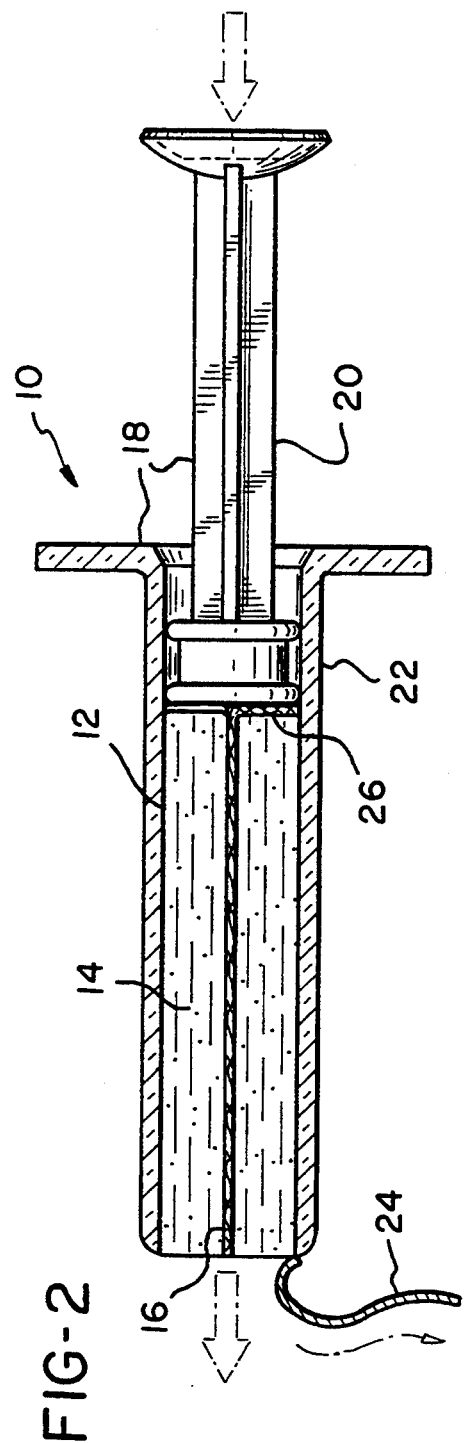

WOUND DRESSING HAVING A CYLINDRICAL SHAPE FOR DEEP WOUNDS

This application is a continuation of application Ser. No. 07/996,013, filed Dec. 23, 1992 (now abandoned).

BACKGROUND OF THE INVENTION

The present invention generally relates to a wound dressing and, more particularly, to a wound dressing comprising a hydrogel material substantially in the form of a cylinder for insertion and removal from a deep wound.

Secreting skin wounds, such as decubitus ulcers and open surgical wounds, have long presented a medical challenge in keeping such wounds sterile and relatively dry. The accumulation of wound exudate, such as blood, pustulation, and other wound fluids, in wound crevices, promotes growth of bacteria and crusted organisms which cause infection and delay the healing process. Such wound exudate may also cause maceration of tissue adjacent the wound and support infection thereof. However, since it is often desirable to allow a wound to heal in a slightly "moist" or occlusive state, which is believed to accelerate healing, excess wound exudate must be removed. If excess wound exudate remains on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all the exudate as that would result in a "dry" wound resulting in a slower healing process.

The art is replete with wound and/or surgical dressings for treating skin lesions, such as decubitus ulcers and open surgical wounds. For example, Mason, Jr. et al, U.S. Pat. No. 4,393,048, disclose a hydrogel wound treatment composition which dries to a powder after it is introduced into an open, draining wound to absorb wound exudate. However, dry hydrogel deteriorates as the wound fluids are absorbed resulting in lumping and uneven application. Additionally, such deteriorated lumps are difficult to remove from a wound site without damaging new cell tissue at the wound site. Furthermore, the progress of wound healing cannot be determined without removing, at least partially, the wound dressing from the wound site.

Aqueous moisture absorbing materials, such as a hydrogel material with a polyethylene glycol liquid curing agent as disclosed in Spence, U.S. Pat. No. 4,226,232, are easier to remove from the wound site, but cannot be sterilized by irradiation due to the formation of free radicals within the aqueous material. Another aqueous absorbing material used to absorb wound exudate is an hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

Nor are existing wound dressings conducive for healing extremely deep wounds. It is not uncommon for certain deep wounds to extend down to the bones or tendons, most of which are typically characterized as stage 3 or stage 4 wounds. The most severe wounds in terms of depth are characterized as stage 4 wounds, and oftentimes have a shape resembling a cylinder or the like. For example, such a wound may be caused by a bullet or a puncture from large equipment or glass. However, known wound dressings do not facilitate the healing of such deep wounds as exemplified by the wound dressings in Mason, Jr. et al, Spence, and Rawlings et al which are designed for treating surface wounds. Moreover, existing filler gel packs used to temporarily fill such deep wounds break apart in fragments upon removal from the wound. These filler gel packs are also difficult to wash out from the healing wound since there is a tendency for the filler material to adhere to the new cell tissue forming on the surface of the wound.

Accordingly, there is a need for a wound dressing which is especially conducive for deep wounds. There is also a need for a wound dressing for a deep wound which may be inserted and removed from a draining wound having a cylindrical shape and which contains an exudate absorbing composition. Finally, there is a need for a wound dressing for a deep wound which may be removed neatly as a single piece without adhering to the new cell tissue of the wound.

SUMMARY OF THE INVENTION

The present invention meets the above-identified needs by providing a wound dressing especially adapted for deep wounds. The term "deep wound," as referenced herein, is defined as those wounds which extend down below the surface of the skin and, in some instances, to the bones or tendons. Those types of wounds extending to the bones and tendons are typically characterized as stage 3 or stage 4 wounds, of which the most severe wounds in terms of depth are characterized as stage 4 wounds. The materials and design of the present wound dressing facilitates the healing of such deep wounds.

In accordance with one aspect of the invention, a wound dressing adapted to be inserted into a deep wound found on a patient is provided. The wound dressing comprises a hydrogel material capable of absorbing wound exudate emitted by the deep wound in which it is disposed. Preferably, the hydrogel material is substantially in the form of a cylinder. The term "cylinder" as used herein is meant to encompass annular and oblong shapes having very small cross-sectional areas to very large cross-sectional areas depending upon the type of wound for which the dressing is applicable. Further, a support layer is mounted within the cylinder for purposes of providing support for the hydrogel material in the wound dressing. The support layer may extend outwardly from an end of the cylinder of hydrogel material so as to provide a pull tab by which the wound dressing can be removed from the deep wound. In addition, the support layer can extend through the entire length of the cylinder as well as outwardly from an end thereof so as to provide a pull tab by which the wound dressing can be removed from the deep wound.

In accordance with another aspect of the invention, a wound dressing product is provided. The wound dressing product comprises a wound dressing adapted to be inserted into a deep wound found on a patient. Preferably, the wound dressing includes a hydrogel material capable of absorbing wound exudate emitted by the wound and the hydrogel material is substantially in the form of a cylinder. Additionally, a support layer is mounted within the cylinder for purposes of providing support for the hydrogel material in the wound dressing. Further, the wound dressing product comprises means for inserting and removing the wound dressing from the deep wound without inhibiting the healing thereof. The preferred inserting/removing means comprises a syringe adapted to inject and withdraw the cylinder of the hydrogel material into and from the deep wound.

Accordingly, it is an object of the present invention to provide a wound dressing especially conducive for deep wounds; it is also an object of the invention to provide a wound dressing for a deep wound which may be inserted and removed from a draining wound having a cylindrical shape and which contains an exudate absorbing composition; and, it is also an object of the present invention to provide a wound dressing for a deep wound which may be removed neatly as a single piece without adhering to the new cell tissue of the wound. Other objects and advantages of the invention will be apparent from the following detailed description, the accompanying drawings and the appended claims.

BRIEF DESCRIPTION OF THE DRAWINGS

FIG. 1 is a perspective view of the wound dressing contained in a dispensing syringe in accordance with the invention;

FIG. 2 is a side view of the wound dressing and dispensing syringe taken along view line 2—2 in FIG. 1;

DETAILED DESCRIPTION OF THE PREFERRED EMBODIMENT

Figure 3:
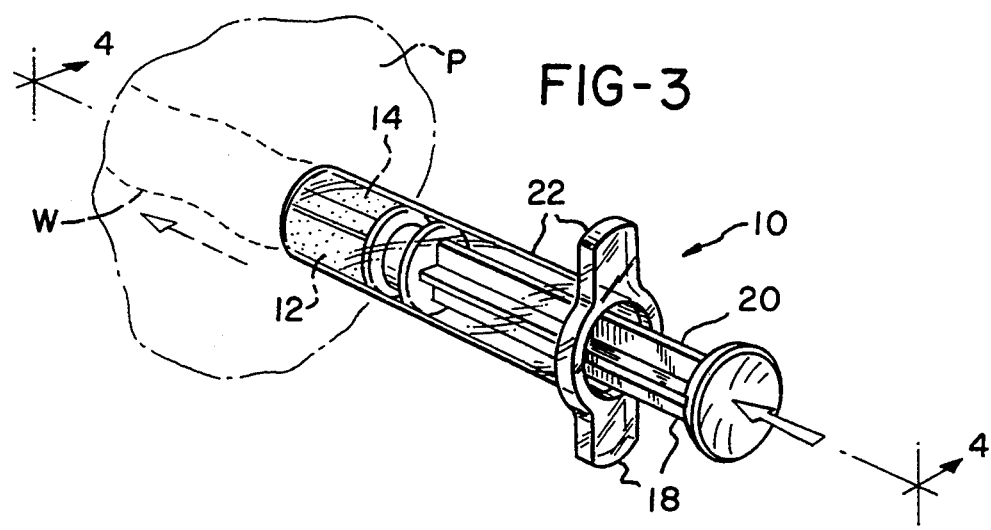
FIG. 3 is a perspective view of the wound dressing partially inserted into a deep wound on the patient's body.

Referring now collectively to FIGS. 1 and 2, a wound dressing product generally designated by reference numeral 10 is depicted. The wound dressing product 10 is adapted to be inserted into a deep wound W (FIG. 3) found on a patient P in a hospital environment. Preferably, the wound dressing product 10 comprises a wound dressing, generally designated by reference numeral 12, which is adapted to be inserted into the deep wound W found on the patient P. As those skilled in the art will appreciate, the size of the wound dressing 12 may be varied as required by end users. For example, the wound dressing 12 can be made to have a wide variety of cross-sectional areas and lengths without departing from the scope of the invention.

The wound dressing 12 preferably includes a hydrogel material 14 capable of absorbing wound exudate emitted by wounds typically found on patients. In addition, the preferred hydrogel material 14 is substantially in the form of a cylinder. As stated previously, the cylinder shape, as used herein, is meant to encompass annular and oblong shapes having very small cross-sectional areas to very large cross-sectional areas depending upon the type of wound for which the dressing is applicable. The wound dressing 12 also comprises a support layer 16 mounted within the cylinder of hydrogel material 14 for purposes of providing support for hydrogel material 14 in the wound dressing 12. More specifically, the hydrogel material 14 remains intact more readily when the support layer 16 is included in the wound dressing 14.

The wound dressing product 10 preferably includes means for inserting and removing the wound dressing 12 from the deep wound W without inhibiting the healing thereof. As shown in FIGS. 1 and 2, the inserting/removing means comprises a syringe device collectively designated as 18 and individually by its components hereinafter. While FIGS. 1 and 2 depict the syringe 18 for inserting and removing the wound dressing 12 into and from the deep wound W, those skilled in the art should understand that other devices capable of inserting and/or removing the wound dressing 12 may be used without departing from the scope of the invention. Additionally, a user, such as a nurse, may manually insert the wound dressing 12 into the deep wound W and thereafter, manually remove it from the patient's body when desired.

The syringe 18 includes a plunger 20 and corresponding housing 22 together which provide the wound dressing 12 with a sterile package and means by which it can be inserted and withdrawn in and from the deep wound W. Additionally, the wound dressing product 10 comprises a release liner 24 which covers the exposed end of the wound dressing 12 as it is stored in the housing 22 of the syringe 18. The release liner 24 is peeled away by the user prior to insertion of the wound dressing 12 into the deep wound W. The inclusion of the release liner 24 ensures sterility of the wound dressing 12 prior to use.

Figure 4:
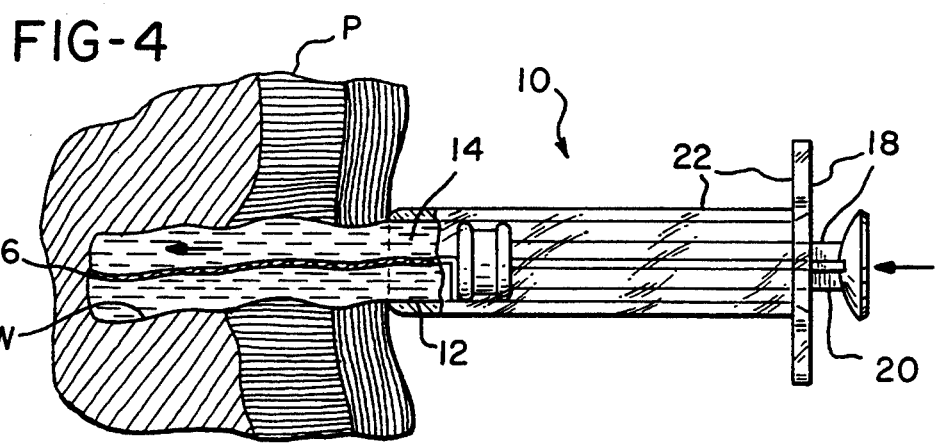
FIG. 4 is a side view of the wound dressing taken along view line 4—4 in FIG. 3.

Reference is now made collectively to FIGS. 3 and 4 which illustrate the wound dressing product 10 as the wound dressing 12 is being inserted into the deep wound W. As seen in FIG. 3, the user pushes against the plunger 20 of the syringe 18, thereby inserting the wound dressing 12 into the deep wound W on the patient P. It is preferable for the wound dressing 12 to completely fill the void created by the deep wound W so as to promote effective healing and to absorb a substantial amount of the wound exudate emitted by the deep wound W. FIG. 4, which is taken along view line 4—4 in FIG. 3, illustrates such a wound dressing. Those skilled in the art, however, will appreciate that the wound dressing 12 can be tailored to the size and depth of the deep wound W, either at the manufacturing stage or by slicing and/or carving the manufactured wound dressing 12 prior to insertion.

Figure 5:
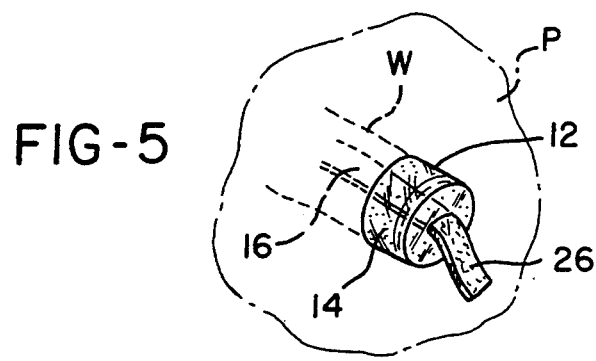
FIG. 5 is a fragmentary perspective view of the wound dressing after it has been inserted into the deep wound.

FIG. 5 illustrates the wound dressing 12 comprising the hydrogel material 14 in the form of a cylinder as it appears mounted within the deep wound W in the patient P. As seen in FIG. 5, the wound dressing 12 is provided with the support layer 16 which extends outwardly from an end of said cylinder so as to provide means by which the wound dressing 12 can be removed from the deep wound W. Such means is depicted in the form of a pull tab 26 which can be grasped by the user to remove the wound dressing 12 from the body of the patient P. Most preferably, the support layer 16 extends through the entire length of the cylinder of the hydrogel material 14 in addition to outwardly from an end thereof so as to provide maximum support for the hydrogel material 14 and to provide the pull tab 26 for easy removal of the wound dressing 12.

Figure 6:
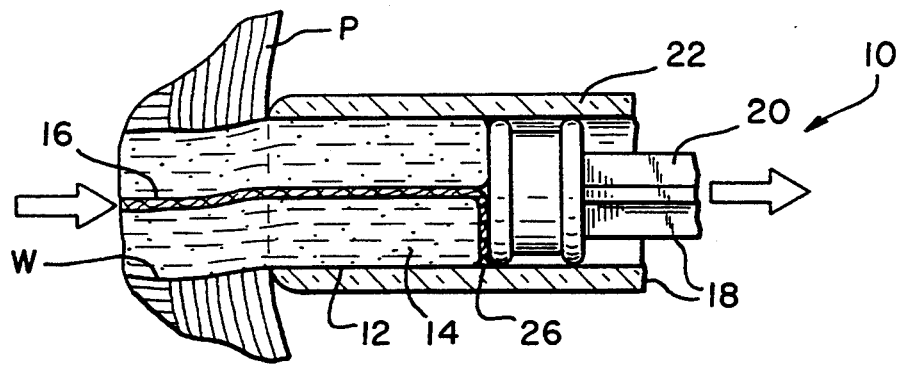
FIG. 6 is a side view of the wound dressing as it is being removed by the dispensing syringe.

Referring now to FIG. 6, a procedure by which the wound dressing 12 can be removed from the deep wound W using the syringe 18 is illustrated. Specifically, the housing 22 of the syringe 18 is mounted over the exposed wound dressing 12 so as to allow the plunger 20 to withdraw the wound dressing 12 by means of the suction or vacuum created by the plunger 20 in the housing 22. Such an operation is very typical of syringes and other similar devices which are used to withdraw fluids and gels from reservoirs.

Since the exposed portion of the wound dressing 12 is not subjected to substantial amounts of wound exudate, the hydrogel material 14 will not swell, thus allowing the housing 22 of the syringe 18 to fit over at least that portion of the wound dressing 12. It should be understood that the hydrogel material disposed in the deep wound W may swell upon absorption of wound exudate to a point at which suction by the syringe 18 into its housing 22 is precluded. That portion, however, which is drawn into the syringe 18 is sufficient to pull the remaining portion of the wound dressing 12 from the deep wound W.

The support layer 16 of the present invention is preferably in the form of a thin, flexible gauze-like structure suitable for use in the treatment of wounds on a patient. Preferably, the hydrogel material 14 of the wound dressing 12 is impregnated in the support layer 16 to provide support therefor. While those skilled in the art will appreciate the difficulty in illustrating the presence of the hydrogel material 14 in the support layer 16, it should be understood that the hydrogel material 14 is preferably completely impregnated in the interstices of the support layer 16. To that end, it is preferable for the support layer 16 to be formed of any material capable of supporting the hydrogel material 14. Those skilled in the art will appreciate that materials having interstices within which materials may be impregnated are particularly suitable for such purposes. In that regard, the support layer 16 is preferably formed from a material selected from the group consisting of fabrics, natural fibers, synthetic fibers, cellulose derivatives and combinations thereof. These preferred materials provide a sufficient support matrix for impregnation of the hydrogel material 14. Most preferably, the support layer 16 comprises a gauze material.

The wound dressing 12 can be removed from the wound in which it is disposed in a non-destructive manner in that the wound dressing 12 does not adhere to the new cell tissue forming in the healing deep wound W. The wound dressing 12 also does not break apart into fragments or lumps, but rather, can be removed substantially as a single piece. Such features have not been present in past wound dressings. These features are largely attributed to the hydrogel material 14 from which the wound dressing 12 is substantially formed. More particularly, the preferred hydrogel material 14 is formed from an aqueous mixture of polyhydric alcohol, an aliphatic diisocyanate terminated prepolymer, polyethylene oxide based diamine and sodium chloride. Preferably, the polyhydric alcohol is selected from the group consisting of polypropylene glycol, polyethylene glycol and glycerine.

The resulting hydrogel material 14 is a highly absorbent material capable of retaining large amounts of wound exudate, thereby rendering it very suitable for use in wound dressings. By forming the hydrogel material 14 from the aforementioned aqueous mixture, the wound dressing 12 remains intact as it absorbs wound exudate from the wound. Moreover, the hydrogel material 14 does not adhere or stick to the wound thereby allowing for easy removal of the wound dressing 12 substantially as a single piece. Additionally, the biocompatibility of the hydrogel material 14 within the wound is extremely favorable. Thus, the hydrogel material 14 provides a bio-compatible, non-irritating, fluid absorbing, bacterial protective, cushioning, skin-like media in and over the wound site.

Those skilled in the art will appreciate that a wide variety of aliphatic diisocyanates may be used in accordance with the invention including but not limited to hexamethylene diisocyanate, isophoronediisocyanate, tetramethylene diisocyanate and decamethylene diisocyanate. The preferred aliphatic diisocyanate terminated prepolymer, however, is an isophoronediisocyanate terminated prepolymer based on polyols containing more than about 40% polyethylene oxide and having an isocyanate content of about 3% by weight. The molecular weight of the isophoronediisocyanate terminated prepolymer is preferably in a range from about 1500 to about 8000 and most, preferably, from about 4000 to about 5000. The polyethylene oxide based polyamine is preferably a polyethylene oxide based diamine having a molecular weight in a range from about 200 to about 6000 and most preferably, about 2000. It is also preferable that the aliphatic diisocyanate terminated prepolymer and the polyethylene oxide based polyamine have a stoichiometric ratio of about 1:1. Those skilled in the art will appreciate that all of the constituents with the preferred hydrogel material may be readily synthesized or purchased commercially neither of which is more preferred.

It has been found that a more preferred hydrogel material 14 is formed from an aqueous mixture including from about 0% to about 90% by weight polyhydric alcohol; from about 6% to about 60% by weight aliphatic diisocyanate terminated prepolymer; from about 4% to about 40% by weight polyethylene oxide based polyamine; up to about 2% by weight sodium chloride; and the balance water. A more preferred hydrogel composition for forming the hydrogel material 30 is formed from a mixture comprising from about 15% to about 30% by weight polypropylene glycol; from about 8% to about 14% by weight isophoronediisocyanate terminated prepolymer; from about 5% to about 10% by weight polyethylene oxide based diamine; and up to about 1% by weight sodium chloride; and the balance water. Most preferably, the hydrogel material 14 is formed from a mixture comprising: (a) from about 16% to 17% by weight polypropylene glycol; (b) from about 10% to 12% by weight isophoronediisocyanate terminated prepolymer; (c) from about 7% to 9% by weight polyethylene oxide based diamine; (d) about 0.5% to 1% by weight sodium chloride; and (e) the balance water.

The aforementioned preferred hydrogel compositions provide a wound dressing 12 having the desired properties of excellent biocompatibility and exudate absorption properties without adhering to the wound. However, other materials having such characteristics, including but not limited to the aforementioned hydrogel compositions, may be used to form the hydrogel material 14 in accordance with the present invention.

The wound dressing 12 of the invention may be formed in a variety of ways including but not limited to pouring the uncured hydrogel material 14 into a mold having the cylindrical shape and disposing the support layer 16 therein as desired. Thereafter, the hydrogel material 14 is allowed to cure to a gel form, after which it is packaged in the syringe 18 as depicted in FIGS. 1 and 2. Those skilled in the art will appreciate that other process techniques may be used to form the wound dressing 12 without departing from the scope of the invention.

With the present invention, a wound dressing especially conducive for deep wounds which can be inserted and removed from a draining wound having a cylindrical shape or a shape in which a cylindrical wound dressing can be disposed is provided. Further, the invention provides wound dressing capable of absorbing large amounts of wound exudate while also having the ability to be removed neatly as a single piece without adhering to the new cell tissue of the wound. Such features provide significant advantages over those wound dressings used for similar purposes in the past.

Having described the invention in detail and by reference to preferred embodiments thereof, it will be apparent that modifications and variations are possible without departing from the scope of the invention which is defined in the appended claims. For example, the wound dressing 12 can be inserted and withdrawn from the deep wound W manually or by means of a device other than the syringe 18 depicted in FIGS. 1–4.

What is claimed is:

1. A wound dressing product comprising:
   a wound dressing adapted to be inserted into a deep wound found on a patient, said wound dressing including
   a hydrogel material capable of absorbing wound exudate emitted by said wound, said hydrogel material being substantially in the form of a cylinder;
   a support layer mounted within said hydrogel material for purposes of providing support for said hydrogel material in said wound dressing, said support layer extending through the entire length of said hydrogel material and outwardly from an end thereof so as to provide a pull tab by which said wound dressing can be removed from said deep wound, said support layer including interstices within which said hydrogel material is impregnated; and
   means for inserting and removing said wound dressing from said deep wound without inhibiting the healing thereof, said means for inserting and removing said wound dressing comprising a syringe having an open end and including a movable plunger adapted to inject and withdraw said cylinder of said hydrogel material through said open end into and from said deep wound by movement of said movable plunger.

2. The wound dressing product of claim 1 wherein said hydrogel material is formed from an aqueous mixture comprising:
   (a) from about 15% to about 30% by weight polyhydric alcohol;
   (b) from about 8% to about 14% by weight isophoronediisocyanate terminated prepolymer;
   (c) from about 5% to about 10% by weight polyethylene oxide based diamine;
   (d) up to about 1% by weight sodium chloride; and
   (e) the balance water.

3. The wound dressing product of claim 1 wherein said hydrogel material is formed from an aqueous mixture comprising:
   (a) from about 16% to 17% by weight polypropylene glycol;
   (b) from about 10% to 12% by weight isophoronediisocyanate terminated prepolymer;
   (c) from about 7% to 9% by weight polyethylene oxide based diamine;
   (d) about 0.5% to 1% by weight sodium chloride; and
   (e) the balance water.

4. The wound dressing product of claim 3 wherein said isophoronediisocyanate terminated prepolymer is based on polyols containing more than about 40% polyethylene oxide and having an isocyanate content of about 3% by weight.

5. The wound dressing product of claim 1 wherein said support layer is formed from a fabric material.

6. The wound dressing product of claim 1 wherein said support layer comprises a gauze material.

7. The wound dressing product of claim 1 wherein said hydrogel material is formed from an aqueous mixture comprising:
   (a) from about 0% to about 90% by weight polyhydric alcohol;
   (b) from about 6% to about 60% by weight aliphatic diisocyanate terminated prepolymer;
   (c) from about 4% to about 40% by weight polyethylene oxide based polyamine;
   (d) 0% to about 2% by weight sodium chloride; and
   (e) the balance water.

8. The wound dressing product of claim 7 wherein said polyhydric alcohol is selected from the group consisting of polypropylene glycol, polyethylene glycol and glycerine.

9. The wound dressing product of claim 1 including a release liner covering the open end of said syringe.

10. The wound dressing product of claim 1 wherein said support layer is formed from a natural fiber material.

11. The wound dressing product of claim 1 wherein said support layer is formed from a synthetic fiber material.

12. The wound dressing product of claim 1 wherein said support layer is formed from a cellulose derivative material.

* * * * *